(12) United States Patent
Schellenberg et al.

(10) Patent No.: US 11,279,983 B2
(45) Date of Patent: Mar. 22, 2022

(54) **FUNGAL STRAIN OF THE GENUS *TRICHODERMA* AND METHOD FOR PROMOTING PLANT GROWTH**

(71) Applicant: HOCHSCHULE ANHALT, Köthen (DE)

(72) Inventors: Ingo Schellenberg, Dessau-Rosslau (DE); Jörg Geistlinger, Heteborn (DE)

(73) Assignee: Hochschule Anhalt, Köthen (DE)

( * ) Notice: Subject to any disclaimer, the term of this patent is extended or adjusted under 35 U.S.C. 154(b) by 0 days.

(21) Appl. No.: 16/980,075

(22) PCT Filed: Mar. 12, 2019

(86) PCT No.: PCT/DE2019/000074
§ 371 (c)(1),
(2) Date: Sep. 11, 2020

(87) PCT Pub. No.: WO2019/174664
PCT Pub. Date: Sep. 19, 2019

(65) Prior Publication Data
US 2021/0244032 A1    Aug. 12, 2021

(30) Foreign Application Priority Data

Mar. 15, 2018 (DE) .................... 10 2018 002 234.0

(51) Int. Cl.
*C12Q 1/6895* (2018.01)
*A01N 63/38* (2020.01)
*C12N 1/14* (2006.01)
*C12R 1/885* (2006.01)

(52) U.S. Cl.
CPC .......... *C12Q 1/6895* (2013.01); *A01N 63/38* (2020.01); *C12N 1/145* (2021.05); *C12R 2001/885* (2021.05)

(58) Field of Classification Search
CPC ...... A01N 63/38; C12N 1/145; C12Q 1/6895; C12R 2001/885
USPC ...................................................... 504/117
See application file for complete search history.

(56) References Cited

U.S. PATENT DOCUMENTS

| | | |
|---|---|---|
| 6,475,772 B1 | 11/2002 | Kalra et al. |
| 6,808,917 B1 | 10/2004 | Johnson |
| 6,890,530 B2 * | 5/2005 | Hermosa Prieto ..... A01N 63/38 424/93.5 |

FOREIGN PATENT DOCUMENTS

| | | |
|---|---|---|
| CN | 102505010 A | 6/2012 |
| EP | 1279335 A1 | 1/2003 |
| WO | WO 2004/089831 A2 | 10/2004 |
| WO | WO 2010/091337 A1 | 8/2010 |
| WO | WO 2011/032281 A1 | 3/2011 |

OTHER PUBLICATIONS

International Search Report issued by the European Patent Office in International Application PCT/DE2019/000074 dated Jul. 4, 2019.
U. Yadav et al. "Biodegradation of sulfosulphuron in agricultural soil by *Trichoderma* sp." Letters in Applied Microbiology, GB, vol. 59, No. 5, Aug. 13, 2014 (Aug. 13, 2014), pp. 479-486.
Dominik Skoneczny et al. "Genetic diversity of *Trichoderma atroviride* strains collected in Poland and identification of loci useful in detection of within-species diversity" Folia Microbiologica., vol. 60, No. 4, Mar. 20, 2015 (Mar. 20, 2015), pp. 297-307.
B. P. Singh "Molecular Markers Used in Fungal Diversity Analysis: An Overview" Choudhury H, editor. Bology, biotechnology and sustainable development. Delhi: Research India Publication; (2015), pp. 167-182.
Joerg Geistlinger et al. "SSR Markers for *Trichoderma virens*: Their Evaluation and Application to Identify and Quantify Root-Endophytic Strains" Diversity 2015, 7, pp. 360-384.
Conrad L. Schoch et al. "Nuclear ribosomal internal transcribed spacer (ITS) region as a universal DNA barcode marker for Fungi" PNAS vol. 109, No. 16 pp. 6241-6246.

\* cited by examiner

*Primary Examiner* — Jennifer M. H. Tichy
(74) *Attorney, Agent, or Firm* — Ursula B. Day, Esq.

(57) ABSTRACT

A fungal strain of the genus *Trichoderma* with the designation HSA12 and compositions that contain said fungal strain or spores thereof is disclosed. The fungal strain or spores thereof are promoting stabilizing plant growth, increasing the yields of crops, inoculating soil, roots and/or above-ground plant parts with the fungal strain or spores with compositions containing said fungal strain or spores thereof, to increase the efficiency of nutrient intake and to improve the stress tolerance of crops as well as improving the structure and health of the soil or for decontaminating or remediating soil or a body of water and for stabilizing or reestablishing endangered or desired wild plant populations. Also disclosed is a set of primer pairs for amplifying microsatellite loci of the genome of the fungal strain in order to determine molecular markers and to identify the fungal strain. A method for determining the fungal strain is also disclosed.

10 Claims, 6 Drawing Sheets
Specification includes a Sequence Listing.

SEQUENCE LISTING

<160> NUMBER OF SEQ ID NOS: 45

<210> SEQ ID NO 1
<211> LENGTH: 20
<212> TYPE: DNA
<213> ORGANISM: Trichoderma sp. 'HSA12'

<400> SEQUENCE: 1
cggatgtgag acgcaatatg                                                 20

<210> SEQ ID NO 2
<211> LENGTH: 20
<212> TYPE: DNA
<213> ORGANISM: Trichoderma sp. 'HSA12'

<400> SEQUENCE: 2
caacagcgaa gtgttgatgg                                                 20

<210> SEQ ID NO 3
<211> LENGTH: 20
<212> TYPE: DNA
<213> ORGANISM: Trichoderma sp. 'HSA12'

<400> SEQUENCE: 3
tcaacttcgc cctcattttc                                                 20

<210> SEQ ID NO 4
<211> LENGTH: 20
<212> TYPE: DNA
<213> ORGANISM: Trichoderma sp. 'HSA12'

<400> SEQUENCE: 4
cgatctcgaa gctgacacag                                                 20

<210> SEQ ID NO 5
<211> LENGTH: 20
<212> TYPE: DNA
<213> ORGANISM: Trichoderma sp. 'HSA12'

<400> SEQUENCE: 5
gtctggctac attggccttc                                                 20

<210> SEQ ID NO 6
<211> LENGTH: 20
<212> TYPE: DNA
<213> ORGANISM: Trichoderma sp. 'HSA12'

<400> SEQUENCE: 6
agacggaggg ggagattatg                                          20

<210> SEQ ID NO 7
<211> LENGTH: 20
<212> TYPE: DNA
<213> ORGANISM: Trichoderma sp. 'HSA12'

<400> SEQUENCE: 7
tcctcctcaa tcacctttgc                                          20

<210> SEQ ID NO 8
<211> LENGTH: 20
<212> TYPE: DNA
<213> ORGANISM: Trichoderma sp. 'HSA12'

<400> SEQUENCE: 8
tttcccgaag aaatcacagg                                          20

<210> SEQ ID NO 9
<211> LENGTH: 20
<212> TYPE: DNA
<213> ORGANISM: Trichoderma sp. 'HSA12'

<400> SEQUENCE: 9
gccacagaga gaagccagtc                                          20

<210> SEQ ID NO 10
<211> LENGTH: 20
<212> TYPE: DNA
<213> ORGANISM: Trichoderma sp. 'HSA12'

<400> SEQUENCE: 10
gcgtcatgtc cccatctatc                                          20

<210> SEQ ID NO 11
<211> LENGTH: 20
<212> TYPE: DNA
<213> ORGANISM: Trichoderma sp. 'HSA12'

<400> SEQUENCE: 11
tttcttcgtg tttccccatc                                          20

<210> SEQ ID NO 12
<211> LENGTH: 20
<212> TYPE: DNA
<213> ORGANISM: Trichoderma sp. 'HSA12'

<400> SEQUENCE: 12
gacaaagaag ccgaggacag                                          20

<210> SEQ ID NO 13
<211> LENGTH: 20
<212> TYPE: DNA
<213> ORGANISM: Trichoderma sp. 'HSA12'

<400> SEQUENCE: 13
atcaatagac ggggcatacg                                          20

<210> SEQ ID NO 14
<211> LENGTH: 20
<212> TYPE: DNA

<213> ORGANISM: Trichoderma sp. 'HSA12'

<400> SEQUENCE: 14
cgaaaagaga gccaaaaacg				20

<210> SEQ ID NO 15
<211> LENGTH: 20
<212> TYPE: DNA
<213> ORGANISM: Trichoderma sp. 'HSA12'

<400> SEQUENCE: 15
ggagaacgaa gcttgacctg				20

<210> SEQ ID NO 16
<211> LENGTH: 20
<212> TYPE: DNA
<213> ORGANISM: Trichoderma sp. 'HSA12'

<400> SEQUENCE: 16
tataccccgc ctcaacagtc				20

<210> SEQ ID NO 17
<211> LENGTH: 20
<212> TYPE: DNA
<213> ORGANISM: Trichoderma sp. 'HSA12'

<400> SEQUENCE: 17
tggtggtgtg tacgaaatgg				20

<210> SEQ ID NO 18
<211> LENGTH: 20
<212> TYPE: DNA
<213> ORGANISM: Trichoderma sp. 'HSA12'

<400> SEQUENCE: 18
ggcatcgtag cgaagtaagc				20

<210> SEQ ID NO 19
<211> LENGTH: 20
<212> TYPE: DNA
<213> ORGANISM: Trichoderma sp. 'HSA12'

<400> SEQUENCE: 19
tccaaaccct gactgaggtc				20

<210> SEQ ID NO 20
<211> LENGTH: 20
<212> TYPE: DNA
<213> ORGANISM: Trichoderma sp. 'HSA12'

<400> SEQUENCE: 20
agatgcagat cgtcgtgttg				20

<210> SEQ ID NO 21
<211> LENGTH: 20
<212> TYPE: DNA
<213> ORGANISM: Trichoderma sp. 'HSA12'

<400> SEQUENCE: 21
ctgcctctcc agaacactcc				20

<210> SEQ ID NO 22
<211> LENGTH: 20

```
<212> TYPE: DNA
<213> ORGANISM: Trichoderma sp. 'HSA12'

<400> SEQUENCE: 22
cattataagg ggccacaacg                                              20

<210> SEQ ID NO 23
<211> LENGTH: 20
<212> TYPE: DNA
<213> ORGANISM: Trichoderma sp. 'HSA12'

<400> SEQUENCE: 23
tacagcacga agacgctctc                                              20

<210> SEQ ID NO 24
<211> LENGTH: 20
<212> TYPE: DNA
<213> ORGANISM: Trichoderma sp. 'HSA12'

<400> SEQUENCE: 24
aacagcgacc aagcataacc                                              20

<210> SEQ ID NO 25
<211> LENGTH: 20
<212> TYPE: DNA
<213> ORGANISM: Trichoderma sp. 'HSA12'

<400> SEQUENCE: 25
ctgtcgagat tgctgctgag                                              20

<210> SEQ ID NO 26
<211> LENGTH: 20
<212> TYPE: DNA
<213> ORGANISM: Trichoderma sp. 'HSA12'

<400> SEQUENCE: 26
atgtactttt ccgcgtccag                                              20

<210> SEQ ID NO 27
<211> LENGTH: 20
<212> TYPE: DNA
<213> ORGANISM: Trichoderma sp. 'HSA12'

<400> SEQUENCE: 27
ttcaacagcg tcaacctcag                                              20

<210> SEQ ID NO 28
<211> LENGTH: 20
<212> TYPE: DNA
<213> ORGANISM: Trichoderma sp. 'HSA12'

<400> SEQUENCE: 28
ccggatttat tttggtggtg                                              20

<210> SEQ ID NO 29
<211> LENGTH: 20
<212> TYPE: DNA
<213> ORGANISM: Trichoderma sp. 'HSA12'

<400> SEQUENCE: 29
catttggggt gggtattctg                                              20

<210> SEQ ID NO 30
```

```
<211> LENGTH: 20
<212> TYPE: DNA
<213> ORGANISM: Trichoderma sp. 'HSA12'

<400> SEQUENCE: 30
attgtcaccg atggaggaag                                              20

<210> SEQ ID NO 31
<211> LENGTH: 33
<212> TYPE: DNA
<213> ORGANISM: Trichoderma sp. 'HSA12'

<400> SEQUENCE: 31
gaagaagaag aagaagaaga agaagaagaa gaa                               33

<210> SEQ ID NO 32
<211> LENGTH: 36
<212> TYPE: DNA
<213> ORGANISM: Trichoderma sp. 'HSA12'

<400> SEQUENCE: 32
tcctcctcct cctcctcctc ctcctcctcc tcctcc                            36

<210> SEQ ID NO 33
<211> LENGTH: 33
<212> TYPE: DNA
<213> ORGANISM: Trichoderma sp. 'HSA12'

<400> SEQUENCE: 33
catcatcatc atcatcatca tcatcatcat cat                               33

<210> SEQ ID NO 34
<211> LENGTH: 45
<212> TYPE: DNA
<213> ORGANISM: Trichoderma sp. 'HSA12'

<400> SEQUENCE: 34
cttcttcttc ttcttcttct tcttcttctt cttcttcttc ttctt                  45

<210> SEQ ID NO 35
<211> LENGTH: 39
<212> TYPE: DNA
<213> ORGANISM: Trichoderma sp. 'HSA12'

<400> SEQUENCE: 35
agtagtagta gtagtagtag tagtagtagt agtagtagt                         39

<210> SEQ ID NO 36
<211> LENGTH: 63
<212> TYPE: DNA
<213> ORGANISM: Trichoderma sp. 'HSA12'

<400> SEQUENCE: 36
gaagtgaagg aagtgaagga agtgaaggaa gtgaaggaag tgaaggaagt gaaggaagtg  60
aag                                                                63

<210> SEQ ID NO 37
<211> LENGTH: 40
<212> TYPE: DNA
<213> ORGANISM: Trichoderma sp. 'HSA12'

<400> SEQUENCE: 37
tttgttttgt tttgttttgt tttgttttgt tttgttttgt                        40
```

```
<210> SEQ ID NO 38
<211> LENGTH: 28
<212> TYPE: DNA
<213> ORGANISM: Trichoderma sp. 'HSA12'

<400> SEQUENCE: 38
gtgtgtgtgt gtgtgtgtgt gtgtgtgt                                        28

<210> SEQ ID NO 39
<211> LENGTH: 24
<212> TYPE: DNA
<213> ORGANISM: Trichoderma sp. 'HSA12'

<400> SEQUENCE: 39
tatatatata tatatatata tata                                            24

<210> SEQ ID NO 40
<211> LENGTH: 25
<212> TYPE: DNA
<213> ORGANISM: Trichoderma sp. 'HSA12'

<400> SEQUENCE: 40
tcaggtcagg tcaggtcagg tcagg                                           25

<210> SEQ ID NO 41
<211> LENGTH: 30
<212> TYPE: DNA
<213> ORGANISM: Trichoderma sp. 'HSA12'

<400> SEQUENCE: 41
cagcagcagc agcagcagca gcagcagcag                                      30

<210> SEQ ID NO 42
<211> LENGTH: 18
<212> TYPE: DNA
<213> ORGANISM: Trichoderma sp. 'HSA12'

<400> SEQUENCE: 42
aggaggagga ggaggagg                                                   18

<210> SEQ ID NO 43
<211> LENGTH: 21
<212> TYPE: DNA
<213> ORGANISM: Trichoderma sp. 'HSA12'

<400> SEQUENCE: 43
tgctgctgct gctgctgctg c                                               21

<210> SEQ ID NO 44
<211> LENGTH: 66
<212> TYPE: DNA
<213> ORGANISM: Trichoderma sp. 'HSA12'

<400> SEQUENCE: 44
agtgccagtg ccagtgccag tgccagtgcc agtgccagtg ccagtgccag tgccagtgcc     60
agtgcc                                                                66
```

```
<210> SEQ ID NO 45
<211> LENGTH: 34
<212> TYPE: DNA
<213> ORGANISM: Trichoderma sp. 'HSA12'

<400> SEQUENCE: 45 atatatat atatatat atatatat atat                                    34
```

FUNGAL STRAIN OF THE GENUS *TRICHODERMA* AND METHOD FOR PROMOTING PLANT GROWTH

CROSS-REFERENCES TO RELATED APPLICATIONS

This application is the U.S. National Stage of International Application No. PCT/DE2019/000074, filed Mar. 12, 2019, which designated the United States and has been published as International Publication No. WO 2019/174664 A1 and which claims the priority of German Patent Application, Serial No. 10 2018 002 234.0, filed Mar. 12, 2018, pursuant to 35 U.S.C. 119(a)-(d) the description of which is hereby incorporated by reference.

STATEMENT REGARDING ELECTRONIC FILING OF SEQUENCE LISTING

A Sequence Listing in ASCII text format, submitted under 37 CFR § 1.821, entitled ST 25 HSA22-17-IP generated on Sep. 14, 2017 and hereby filed via EFS web, is provided in lieu of a paper copy. The Sequence Listing is hereby incorporated by reference in its entirety into the specification for its disclosure.

BACKGROUND OF THE INVENTION

The invention relates to a fungal strain of the genus *Trichoderma* with the designation HSA12 as well as compositions containing this fungal strain or its spores. The invention further relates to the use of the fungal strain or its spores in various methods, for example in a method for promoting and/or stabilizing plant growth and/or for increasing the yields of crops that involve the inoculation of soil, roots and/or above-ground plant parts with the fungal strain or spores or with this fungal strain or compositions containing its spores, inter alia for increasing the efficiency of nutrient uptake and for improving the stress tolerance of crop plants. The invention also relates to the use of the fungal strain or its spores in a method for improving the structure and health of the soil or for decontamination or remediation of contaminated sites in a soil or a body of water and in a method for stabilizing or resettling endangered or desired wild plant populations. In addition, the invention relates to a primer pair set for the amplification of microsatellite loci of the genome of the fungal strain for the development of molecular markers and for the identification of the fungal strain as well as a method for the identification of the fungal strain.

Intensive agriculture consumes non-renewable resources in the form of industrially manufactured mineral fertilizers, for example phosphates, and uses environmentally questionable chemical pesticides, which are often found later as pesticide residues in food. In particular, intensive fertilization with phosphate and nitrogen compounds eutrophicates surface waters through leaching and has serious consequences for ecosystems such as rivers, lakes and coasts, and also contaminates the groundwater. Legislators, both at the national and the European Union (EU) level, are taking countermeasures by tightening the limit values, for example with the National Action Plan: "Sustainable Use of Pesticides" and the amendment to the EU fertilizer regulation. The implementation of these guidelines, which provide for a reduction of pesticides by 30% and mineral fertilizers by up to 70%, is associated with massive yield losses for farmers, which are almost unbearable economically. Therefore, alternative strategies for increasing nutrient efficiency and strengthening plant resistance to biotic and abiotic stress factors in agriculture are urgently needed.

One solution is the use of soil microorganisms. These have numerous unspecific properties, such as reducing nutrient leaching or improving soil structure, which can be attributed to many, if not all, soil microorganisms. However, there are also highly specific properties which can be traced back to symbiotic interactions with plant roots and which can vary widely from species to species and even from strain to strain within a species of soil microorganisms. This includes the mobilization and provision of nutrients, such as phosphate, nitrogen and trace elements, from the soil as well as the induction of resistance and stress defense genes and the increased tolerance to biotic and abiotic stress factors associated therewith.

Until now, in particular the use of fungi of the genus *Trichoderma* as soil microorganisms has been known in this context. *Trichoderma* is a larger genus of fungi with thus far 314 characterizing species. The genus is widespread in biotechnology and is used for enzyme production for the detergent industry and for laboratory analysis. The supply of *Trichoderma* products for horticulture and agriculture is still very transparent, at least in Germany. The corresponding products are mostly sold as so-called soil additives or plant fortifiers, less often as organic fertilizers. These are the products Trichostar®, Trichosan®, Vitalin®. "Promot", Trianum™, "Triprof", "Mycorrmax", Bohealth™, "T-Gro", "Tripol" and "AcTRIvator" as well as some combination products, which additionally contain rhizobacteria. The *Trichoderma* species used in support of crop production are according to the manufacturers' information different strains of *Trichoderma harzianum, Trichoderma virens, Trichoderma asperellum, Trichoderma artroviride* and *Trichoderma koningli* with various, mostly low, spore concentrations in the products.

Some strains, such as the *Trichoderma harzianum* strain T22 used in the Trianum® product, can dissolve minerally bound phosphate, but have no positive effect on root growth. Other manufacturers, such as the company Partner Plant GmbH with its product "Promot", attempt to combine in one product several different strains which affect crops differently and hope to make both positive properties available for crops. However, this is usually not successful because, due to the competition for nutrients and the different suitability of the strains in the given soil types, both strains do not grow consistently, but one of the strains grows faster due to better adaptation to the given conditions and colonizes the roots earlier. In addition, the plant roots select fungal strains in their rhizosphere. If a strain has colonized the root and has triggered, for example, local resistance mechanisms in the root, e.g. by strengthening the plant cell walls through callose accumulation, further strains can only penetrate the root with a delay or not at all. As a result, their positive effects on the plant metabolism do not come into play. Therefore, efficient multiple colonization occurs only if conditions happen to exist under which the different strains grow equally well and reach the roots more or less at the same time, before defense mechanisms are triggered and are physiologically implemented in the roots. This concerns, for example, the period of a few hours from the recognition of the root colonization, the signal recognition by the plant, the transduction of the signal in physiological reactions, to the callose accumulation in the cell walls. The uniform expression of the various effects of different strains is therefore only successful under very rare conditions.

It is therefore in particular the object of the invention to provide an isolate from microorganisms which combines several positive effects on crops.

SUMMARY OF THE INVENTION

As one aspect of the object of the invention a fungal strain of the genus *Trichoderma* with the designation HSA12, which was deposited on Jan. 12, 2018 under the patent deposit number DSM 32722 at the Leibniz Institute DSMZ—German Collection of Microorganisms and Cell Cultures GmbH, or by spores thereof is claimed. This fungal strain is referred to below also as *Trichoderma* species strain HSA12 or abbreviated as T. sp. HSA12. In addition, any composition that includes the named *Trichoderma* species strain HSA12 or spores thereof also represents a solution of the object of the invention. Advantageous developments are recited in the dependent claims. Thus, in addition to the *Trichoderma* species strain HSA12 or its spores, the composition can furthermore include a carrier. In addition, combinations of the *Trichoderma* species strain HSA12 or its spores with other microorganisms and/or synthetic or biological fertilizers and/or additives/adjuvants and carrier materials are also possible in the composition. The combination with other microorganisms mainly affects gram-negative and/or gram positive prokaryotes such as bacteria and archaea. Additional micro-fungi as well as micro-protists, for example Oomycetes, can be added to positively affect plant growth. Mineral nutrients such as nitrogen, phosphorus, potassium and trace elements as well as amorphous silicon are used as synthetic or biological fertilizer additives, and compost extracts and algae extracts and humic adds are used as biological additives. The added additives/adjuvants depend on the form of application. Adhesives, wetting agents and stabilizers are used for coating seeds with vital T. sp, HSA12. Dispersants/emulsifiers, UV protective pigments, preservatives, antifreeze, wetting agents and foam reducers are used with liquid preparations for foliar and soil application, and adhesives, preservatives and stabilizers are used with granules for soil application. The carrier substances used are of mineral origin and are added to the dry preparations as a powder, for example kaolin, bentonite, day or diatomaceous earth.

The fungal strain HSA12 is a root endophyte that enters into an endosymbiosis with its host plants, i.e. the fungal hyphae penetrate even deeper tissues of the root cells. Accordingly, the fungus was isolated from the roots of a wild plant in the Central German arid region, but not from the soil, and has a very broad host spectrum. This was confirmed by inoculation tests in the roots of all crops examined so far. By isolating, formulating and then using the fungal isolate in potted and field experiments in comparison to untreated crops, intensive research has shown that HSA12 combines numerous properties that have a positive effect on its host plants:

I. a root-endophytic habit, i.e. HSA12 colonizes plant roots without causing damage symptoms, which is a so-called mycorrhiza, i.e. a form of symbiosis of fungi and plants, in which a fungus is in contact with the fine root system of a plant, with the detection taking place via DNA/polymerase chain reaction (PCR);

II. an enlargement of the root surface, whereby the intracellular/root-endophytic fungal hyphae of the endosymbiosis are joined with the soil mycelium, which results in a higher drought stress tolerance;

III. an improvement of the rhizosphere competence, whereby HSA12 is always detectable in the root region and is not fought by the plant by excreting antifungal substances;

IV. an induction of root growth and thereby improved stability and drought stress tolerance of the host plants, especially in tomatoes and maize;

V. improved nutrient and trace element intake;

VI. Increased yields compared to the untreated controls, especially for tomatoes and maize;

VII. an increased activity of Mn-dependent superoxide dismutase (SOD) in stems and leaves, which results in an increased tolerance to oxidative stress from reactive oxygen species, especially in maize;

VIII. an increase in cold stress tolerance in maize, for example at a root region temperature of 12° C., which leads to increased levels of polyphenol/flavonoid/proline, which are anti-stress metabolites, in stems and leaves and reduced leaf necrosis; and IX. an induction of an early flowering time and an increase in valuable ingredients in the harvested material of crops.

Furthermore, the use of *Trichoderma* sp. HSA12 apparently causes induction of local resistance in the root and systemic resistance in the whole plant and thus a so-called priming of the immanent immune system of the plants;

mobilization of phosphates fixed in minerals, as detectable in the calcium phosphate/hydroxyapatite test, and breakdown of harmful organic substances in the soil and in body of waters, such as phenols, polycyclic hydrocarbons and toxins.

In summary, it can be stated that the *Trichoderma* sp.-strain HSA12 combines numerous positive properties which in this combination are hitherto unique and which do not exist in any other strain. This leads to numerous application possibilities for conventional agriculture, horticulture and vegetable farming as well as organic farming.

The above-mentioned advantages offer the possibility of using the fungal strain or its spores in processes having different objectives.

One aspect of the invention therefore relates to a method for promoting and/or stabilizing plant growth and/or for increasing the yields of crops, which includes inoculation of the sol, the roots and/or the above-ground parts of the plant with the aforementioned *Trichoderma* species strain HSA12 or spores thereof or a composition which includes this fungal strain or spores thereof.

In particular, the inoculation of the soil and/or of the roots with the fungal strain *Trichoderma* sp. HSA12 or its spores mobilizes minerally and/or organically bound phosphate for improving crop nutrition and conserving mineral fertilizers. The application of the fungal strain *Trichoderma* sp. Strain HSA12 or its spores enable the use of natural soil-phosphate reserves, which are not accessible to plant roots because the plant roots are unable to dissolve and absorb phosphate incorporated in minerals. In addition, due to the phytase activity, organically bound phosphate from plant residues, which plants are also unable to absorb, can also be used. The latter suggests greater efficiency with green manure. Due to these two properties, the yields can be kept largely stable even when the quantity of mineral fertilizers is significantly reduced.

In addition, inoculating the soil and/or roots with the fungal strain *Trichoderma* sp. HSA12 or its spores also promotes the root growth of the crop plants, accompanied by an improved absorption of nutrients, trace elements and water by the crop plants which further increases the yields. Root growth also improves the stability and drought stress tolerance of many crop plants, which can be an advantage in extreme weather conditions such as strong winds, heavy rain or drought, in order to meet the challenges of climate change.

Due to the properties of the fungal strain Trichoderma sp. HSA12, such as promoting drought stress tolerance, cold stress tolerance and oxidative stress tolerance of crop plants, in particular by promoting the expression and activity of anti-stress metabolites in the crop plants, plant growth can advantageously take place under abiotic stress. This abiotic stress can be present in the form of drought stress, cold stress and/or oxidative stress. The abiotic stress can be caused, for example, by a too-early or too-late sowing or planting date for the crop plant in relation to the respective region.

In particular, the greater tolerance of the treated crop plants to cold stress is a property that has hitherto not been observed in connection with other fungal strains. As a result, new opportunities open up for cultivating some plant species, such as soy and maize, in cooler latitudes. For example, in the case of maize, the late sowing date in the second week of May had to be observed in Central Europe. This date can be moved up by using Trichoderma sp. HSA12 with the associated increase in cold stress tolerance. In this way, higher yields can also be achieved in cooler latitudes.

Treatment of the crop with the fungal strain Trichoderma sp. HSA12 or its spores also induces or stimulates the plant immune system and activates resistance genes in crops. The treatment also leads to an increase in the general resilience of crops.

The increase in yields is also related to the induction of an early flowering time in crop plants, which was also observed with the above-mentioned inoculation. The increase in valuable ingredients in the harvested crops, such as tomatoes, was also observed.

Another aspect of the invention relates to a method for improving the structure and health of the soil or for decontaminating or remediating contaminated sites of soil or of a body of water containing toxic organic substances, which includes inoculating the soil or the body of water with the fungal strain Trichoderma sp. HSA12 or spores, or with compositions containing the fungal strain or its spores, and cultivating the Trichoderma-species-strain HSA12 and optionally additional strains of the composition in the soil or in the body of water.

An additional aspect of the invention relates to a method for stabilizing or resettling endangered or desired wild plant populations, which includes inoculating the soil, roots and/or above-ground parts of the wild plants with the fungal strain Trichoderma sp. HSA12 or spores or with compositions containing the fungal strain or its spore.

In all of the above-mentioned methods, the fungus must be used as a living culture in the form of vital spores or hyphae capable of reproduction, since the fungal strain can only develop its effect as a living organism.

Trichoderma belongs to the division of Ascomycota (sac fungi), which can particularly easily be cultivated on nutrient media and which are characterized by forming large amounts of vegetative spores during this time. Therefore, there is no impediment to mass production for agriculture.

A particularly preferred embodiment relates to a composition and its use in the methods described above, wherein this composition, in addition to the fungal strain Trichoderma sp. HSA12 includes as another micro-organism a rhizobacterium, with which Trichoderma sp. HSA12 synergistically interacts. This could be observed, for example, for the strain Bacillus amyloliquefaciens FZB42, which is manufactured and sold by the company AbiTEP, Berlin, under the product name RhizoVital. A clear synergism can be seen when plant roots, for example maize and tomato, are individually inoculated with HSA12 or FZB42 and the results are compared with roots inoculated with HSA12 and FZB42. The combination always achieves better results than the individual inoculations. With maize and tomato, this was evidenced by stronger root growth, earlier flowering and, as a result, by a significantly higher yield compared to the plants inoculated with only one culture and to the untreated controls.

With the availability of the complete genome sequence, altogether 39.69 Mb megabase pairs including mitochondrial DNA sequence, the strain can be identified at any time in the environment or in any products. In this context, a further aspect of the invention is a primer pair set for the amplification of microsatellite loci of the genome of the fungal strain for the determination of molecular markers and for the identification of the fungal strain. The respective primer pairs are formed from the primers with the primer sequences SEQ ID NO. 1 and 2; 3 and 4; 5 and 6; 7 and 8; 9 and 10; 11 and 12; 13 and 14; 15 and 16; 17 and 18; 19 and 20; 21 and 22; 23 and 24; 25 and 26; 27 and 28; 29 and 30 listed below. By means of the primer pair set, a marker set for the determination of the fungal strain Trichoderma sp. HSA12 can be amplified, which includes the sequences with the SEQ ID NO. 31 to 45 listed below.

A corresponding method for determining the fungal strain to includes the following method steps
  extracting the DNA from a sample that contains the fungus, e.g. roots, soil or cultures,
  amplifying genome segments as microsatellite loci for determining molecular markers by means of the primer pairs of the primer pair set and the polymerase chain reaction (PCR), and
  determining the fragment length of the respective genome sections, given in base pairs (bp), and/or the type of repeating sequences and/or the respective number of sequence repetitions (repeat number) in the genome sections and comparing the same with the corresponding properties of the fungal strain Trichoderma sp. HSA12.

BRIEF DESCRIPTION OF THE FIGURES OF THE DRAWING

Further details, features and advantages of embodiments of the invention will become evident from the following description of exemplary embodiments with reference to the appended drawings, which show in.

Figure 1:
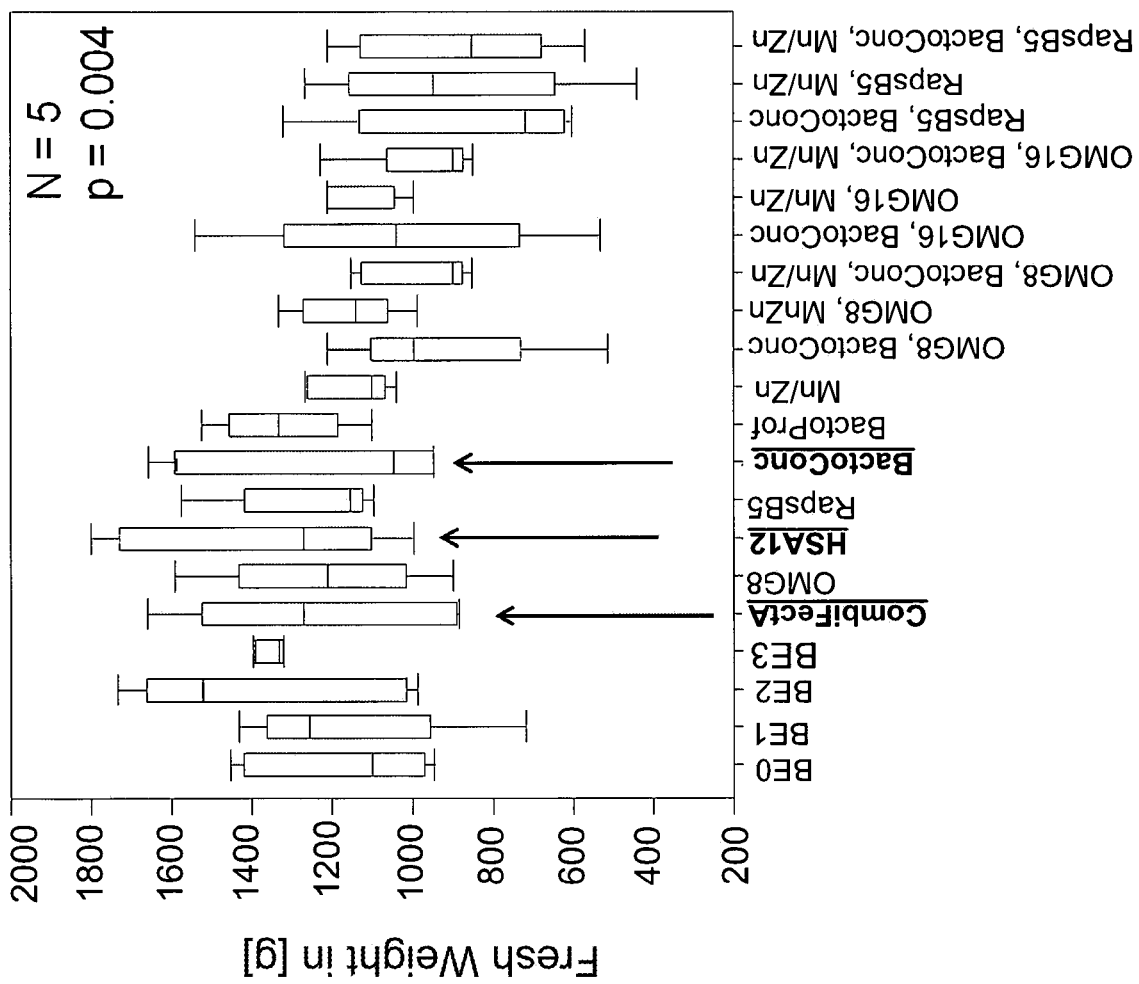
FIG. 1: a bar graph comparing the yields of dwarf tomatoes with and without T. sp. HSA12 treatment.

Table 1 shows, based on a comparison with a known bioeffector product, the induction of root growth and thereby improved stability and drought stress tolerance of the host plants, especially in maize, through inoculation with the fungal strain HSA12 of the genus *Trichoderma*, hereinafter referred to as *Trichoderma* species HSA12 or T. sp. HSA12, wherein the increase is 130 and 190%, respectively.

TABLE 1

|  | Shoot-Biomass | Root Length | Phosphorus content of the Shoot |
|---|---|---|---|
| $NO_3$ + phosphate in solution | 100% (111 g) | 100% (4900 cm) | 100% (24 mg/Plant) |
| $NH_4$ RP | 59 | 126 | 73 |
| $NH_4$RP Trianum ™ | 75 b | 117 | 84 b |
| $NH_4$RP T.sp.HSA12 | 86 ab | 190 b | 78 |

RP = Raw Phosphate
a = not significantly greater than with supplied phosphate;
b = significantly different from comparison value of $NH_4$ RP The induced growth in maize depends on the form of the nitrogen and phosphorus supply. The tests were carried out on low-phosphorus loam soil with 20 mg phosphorus per kg of soil available to the plant. The amount of phosphorus was determined from calcium acetate-lactate extract, abbreviated as CAL extract, as a generally known method for the extraction of phosphorus available to plants. The abbreviation RP stands for rock phosphate. T. sp. HSA12 induces stronger growth than the bioeffector product Trianum™. Unlike Trianum™, the T. sp. HSA12 has no effect on the proportion of phosphorus in the shoot, but induces a strong increase in root growth (190%), which, as evident from the comparison of the respective root lengths, Is significantly stronger than with treatment with Trianum™. This shows that T. sp. HSA12 promotes the development of maize by increasing root growth.

Table 2 shows the respective content of nitrogen N, phosphorus P, potassium K and manganese Mn in the shoot of maize, whereby it becomes evident from Table 2 how this content is influenced by to the inoculation with T. sp. HSA12 and—related to it—by the type of nitrogen and phosphorus supply. The stronger growth-promoting effect of T. sp. HSA12 on the plant compared to the Trianum™ product can be explained by improved access to several nutrients, namely nitrogen N, potassium K and manganese Mn, brought about by increased root growth. Maize has improved nutrient and trace element uptake in particular for nitrogen N and manganese Mn.

TABLE 2

|  | N (mg per Plant) | P (mg per Plant) | K (mg per Plant) | Mn (mg per Plant) |
|---|---|---|---|---|
| $NO_3$ + phosphate in | 100% (289) | 100% (24) | 100% (34) | 100% (0.26) |
| $NH_4$ RP | 93 a | 73 | 70 | 94 a |
| $NR_4$RP Trianum ™ | 109 a | 84 b | 85 b | 111 a |

TABLE 2-continued

|  | N (mg per Plant) | P (mg per Plant) | K (mg per Plant) | Mn (mg per Plant) |
|---|---|---|---|---|
| $NH_4$RP T.sp.HSA12 | 122 ab | 78 | 87 ab | 128 ab |

RP = Raw Phosphate
a = not significantly greater than with supplied phosphate;
b = significantly different from comparison value of $NH_4$ RP

DETAILED DESCRIPTION OF PREFERRED EMBODIMENTS

FIG. 1 shows, with reference to a bar graph, the influence of T. sp. HSA12 on the yield of dwarf tomatoes (Tomato cultivar DwarfTom) compared to the untreated controls in dwarf tomatoes. The yield information is given as the fresh weight of the tomato fruits. The tests were carried out in loess black earth soil without phosphorus fertilization and a pH value of 7.2.

The value N is the sample size per test element. If N=5, this corresponds to a sample size of 5 plants per treatment. The value assigned to the lower-case letter p in the diagram is an indication of the significance level. A value p=0.004, which is significantly smaller than 0.05, indicates a very strong significance.

The abbreviation BE stands for a "BioEffector" for microbial growth promotion. In contrast, BEO is the abbreviation for an untreated control. BE1 refers to Trianum®P, a commercial product from the company Koppert Ltd. from the Netherlands, which contains a *Trichoderma* fungal strain labelled T22. BE2 refers to Proradix, a commercial bacterial product (*Pseudomonas*) from the company Sourcon-Padena GmbH, Tübingen. BE3 refers to the strain FZB42 of the bacterial genus *Bacillus amyloliquefaciens*, which is also manufactured and sold under the name RhizoVital™ by the company AbiTEP Berlin. CombifectA consists of a combination of T. sp. HSA12 in combination with 5 bacilli BactoConc.

OMG8, RapB5 and OMG16 are abbreviations for other *Trichoderma* strains from the University Anhalt as T. sp. HSA12. BactoConc is a bacterial product made from five different *Bacillus* strains, BactoProf is a bacterial product made from different bacteria and additives. Both are products from the company Bactiva GmbH, Straelen. Zinc and manganese (Mn/Zn) are used as trace elements in some samples. Furthermore, mixtures of the above listed components are used. The specification PO applies to all samples, meaning that no additional phosphate fertilization takes place.

When incubated with T. sp. HSA12, a fresh weight of >1700 g was determined. With BE2, it was 1650 mg, with BactoConc 1650 g, with CombifectA>1500 g. Increased tomato yields are obtained compared to the untreated controls.

Figure 2A:
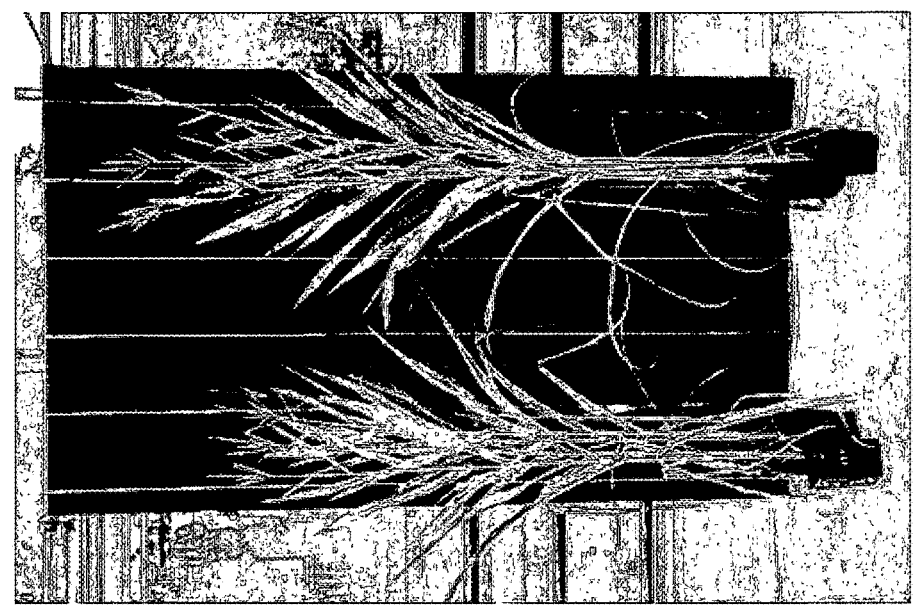
FIGS. 2A-C: the results of potted experiments with differently treated maize plants in form of bar graphs.
Figure 2B:
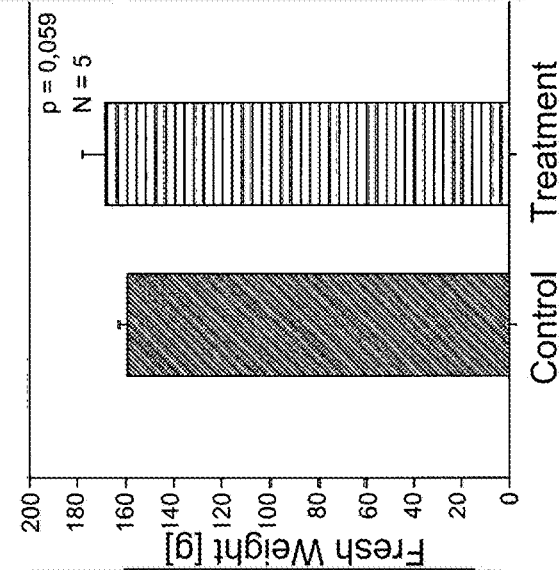
Figure 2C:
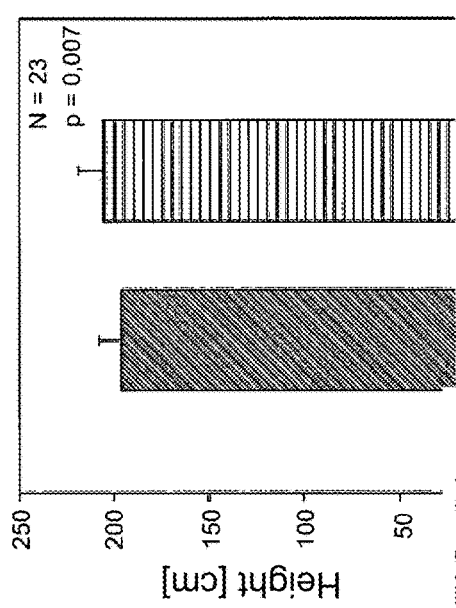
Figure 2D:
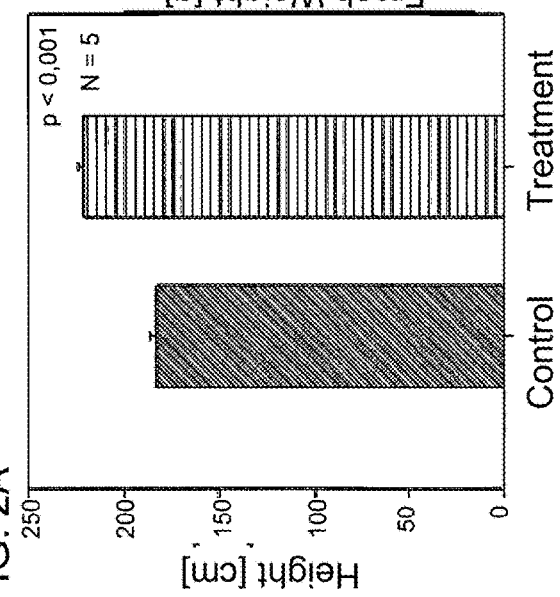
FIG. 2D: the results of potted experiments with differently treated maize plants with reference to a photographic image.

FIGS. 2A to D show the results of a growth test in the form of potted experiments with maize. In these experiments, as the bar graphs in FIGS. 2A to C and the photographic image FIG. 2D show, the influence of *Trichoderma* sp. HSA12 on the height in cm and the fresh weight in grams of the above-ground parts of the maize plant compared with the untreated controls become evident. The value for N indicates the sample size, which is 5 and 23 plants, respectively, while the value for p indicates the level of significance.

The results confirm the significant growth-promoting influence of *Trichoderma* sp. HSA12.

Figure 3:
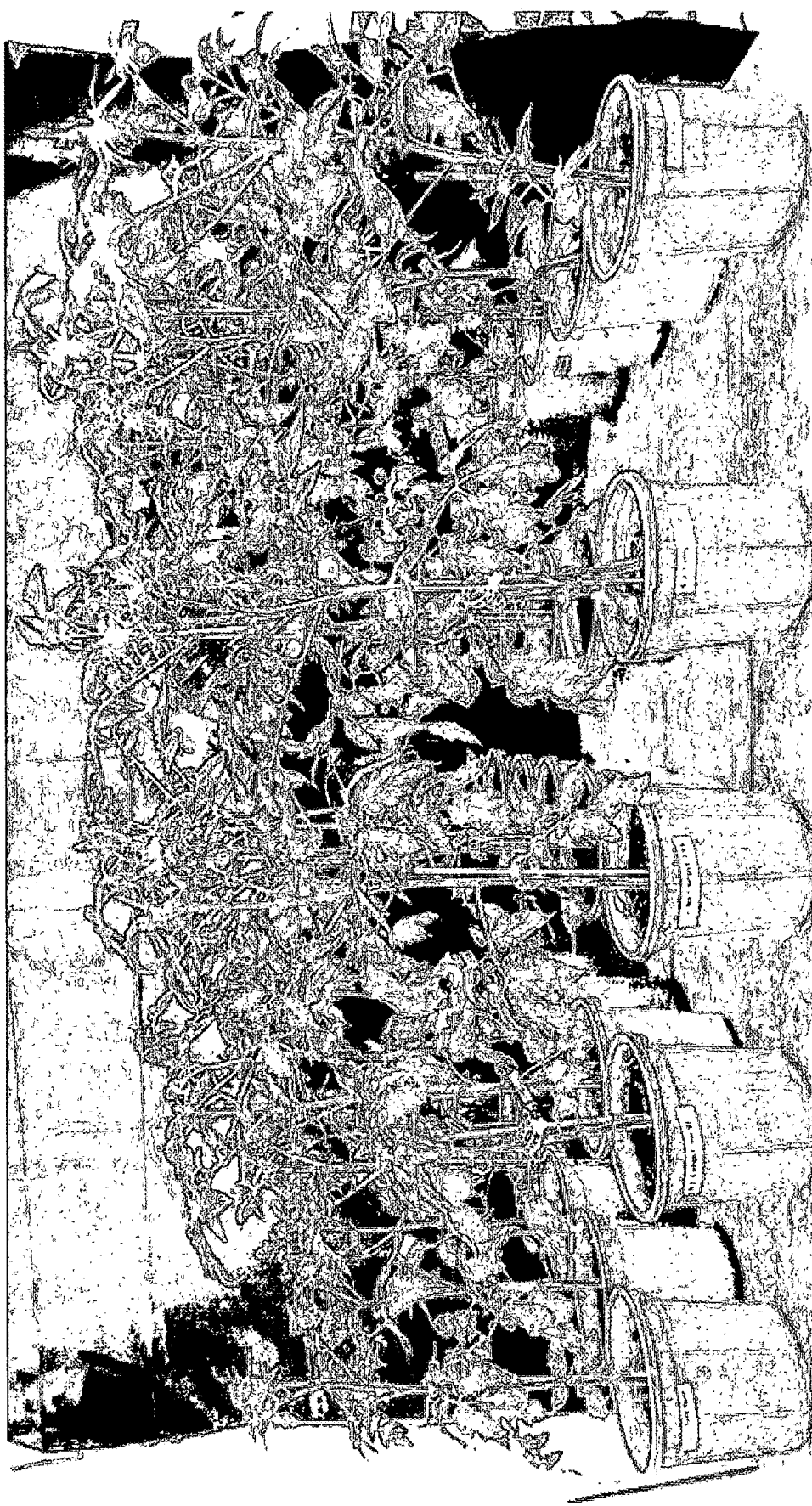
FIG. 3: a photographic image which compares tomato plants after different cultivation conditions at the time of the final harvest.

FIG. 3 shows a photographic image which compares the tomato plants after different cultivation conditions at the time of the final harvest. Unfertilized plants and plants fertilized in compost soil are each cultivated with and without *Trichoderma* sp. HSA12 inoculation. The dry weight of the unfertilized tomato plant without T. sp. HSA12 inoculation was 32.6 g, the dry weight of the unfertilized tomato plant with T. sp. HSA12 inoculation was 49 g. The tomato plant grown without T. sp. HSA12 inoculation on composted soil had a dry weight of 46.2 g, the tomato plant on composted soil with T. sp. HSA12 inoculation had a dry weight of 53 g. In comparison, a plant that was fertilized with dissolved phosphate (triple-superphosphate) had a dry weight of 95.2 g. The latter serves as a positive control for what can only be achieved with complex and environmentally harmful chemical fertilization.

Table 3 shows the change in the defense reactions of maize compared to potted experiments with maize in soil containing nitrate ($NO_3$), with the data being given in percent. The results show that the addition of ammonium ($NH_4^+$) reduces leaf damage and activates protective compounds such as proline, silicon (Si) and superoxide dismutase (SOD). The addition of T. sp. HSA12 produces additional defense compounds, such as ascorbate peroxidase (APX), antioxidants, root SOD and root proline, which is associated with an additional reduction in leaf damage. In comparison, zinc and manganese, which are not approved for organic farming, silicon or "AlgaVyt", an algae product that is very rich in minerals, or Superfifty®, a seaweed extract for use as a growth stimulator in plants, or aqueous extracts from compost, so-called compost tea, are added to the soil or leaves in further controls. The increased activity of Mn-dependent superoxide dismutase (SOD) in stems and leaves results in an increased tolerance to oxidative stress from reactive oxygen species in maize.

conditions is compared in a bar graph. The plants were fertilized with either nitrate ($NO_3^-$) or ammonium ($NH_4^+$). In addition, there was no further addition of trace elements or cultures in the untreated, cooled control noBE. Another control was carried out under uncooled conditions, i.e. at a root temperature of 18° C. The other comparative cultivations for cultivation according to T. sp. HSA12 Inoculation were carried out either with the addition of the trace elements zinc and manganese (Zn, Mn) or Abi02, a *Bacillus* preparation from the company ABITEP GmbH, or BFOD-*Penicillium* (fungus), a preparation from the company Bayer Crop Science.

After the start of the cold period of 14 days with temperatures of 12° C., oxidative leaf damage, namely necrosis, chlorosis and anthocyanin formation, develops rapidly. The leaf damage decreases in the following order:

Abi 02+ZnMn>ZnMn>BFOD+ZnMn>T. sp. HSA12>uncooled control.

The root space temperature of the cooled plants is 12° C. In general, plants treated with ammonium incur less damage than plants treated with nitrate. Only the uncooled plants show less leaf damage than the plants treated with T. sp. HSA12. In other words: The uncooled control naturally has the fewest necroses, but the cultivation after T. sp. HSA12 inoculation, which protects maize very well against damage caused by the cold, shows the second-best results. The protection is better with ammonium fertilization than with nitrate fertilization, as the significantly smaller columns indicate.

Cold stress tolerance in maize increases after the inoculation with T. sp. HSA12, which leads to increased levels of polyphenol/flavonoid/proline as anti-stress metabolites in stems and leaves and reduced leaf necrosis.

Figure 5B:
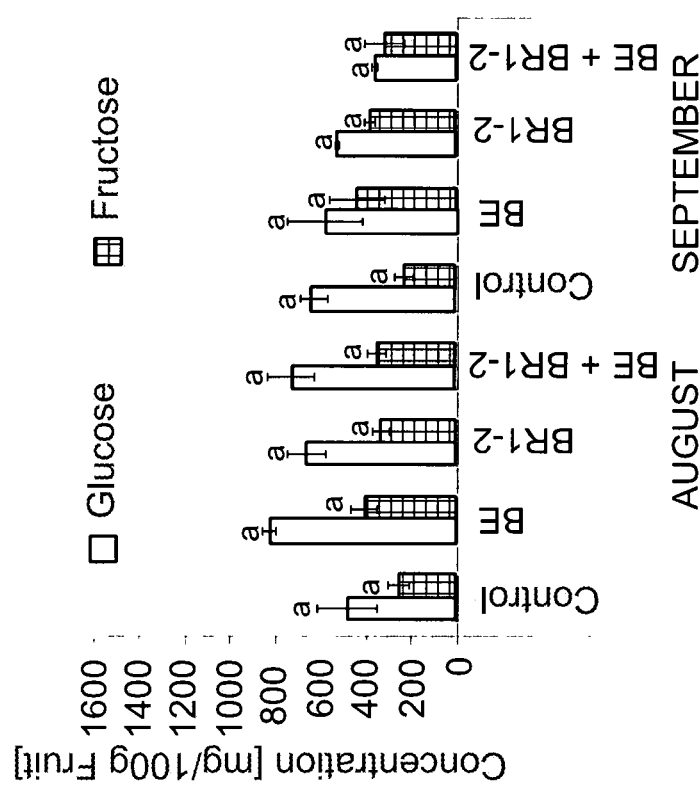
FIGS. 5A-B: bar graphs showing an induction of an early flowering time and the increase in valuable ingredients in the tomato harvest due to the early flowering when Trichoderma sp. HSA12 was added.
Figure 5A:
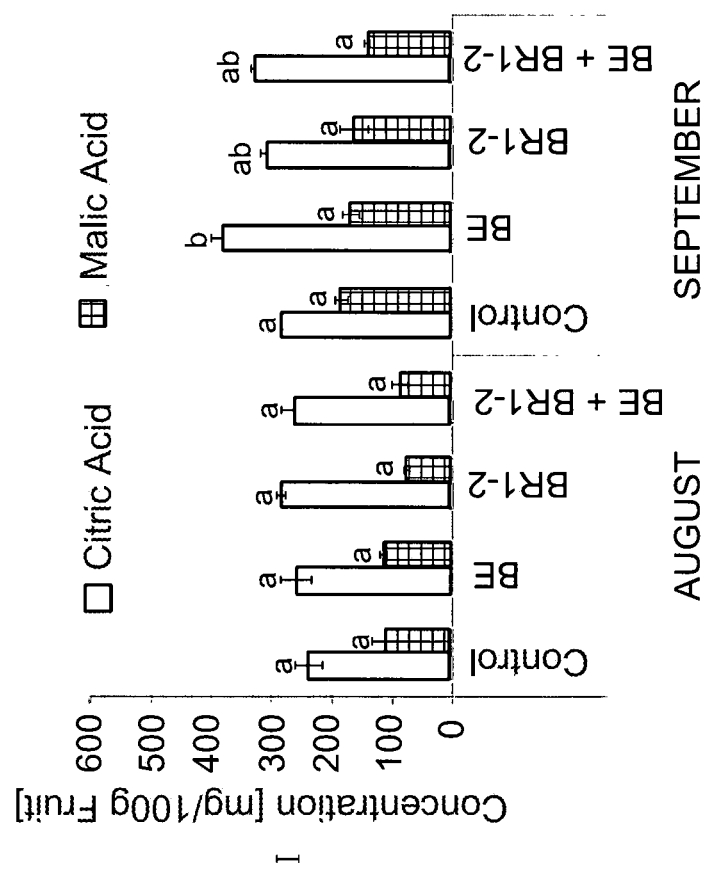

FIGS. 5A and 5B show in form of bar graphs an induction of an early flowering time and the increase in valuable

TABLE 3

| Defense Reaction [% Change compared to $NO_3$— Control] | Only $NH_4^+$ | Soil Treatment | | | Leaf Treatment | | Compost tea |
|---|---|---|---|---|---|---|---|
| | | HSA12 | Zn/Mn | Si | AlgaVyt Zn/Mn | Superfifty ® | |
| Root length | k.A. | k.A. | k.A. | +44 | k.A. | k.A. | k.A. |
| Oxidative Stress | | | | | | | |
| Leaf damage | −17 | −42 | −41 | −33 | −44 | −34 | −45 |
| SOD (Shoot) | +41 | +26 | +15 | +51 | +44 | +60 | +51 |
| SOD (Root) | k.A. | +89 | +95 | +110 | k.A. | k.A. | k.A. |
| APX (Shoot) | k.A. | +47 | +62 | +54 | +54 | +59 | +53 |
| Antioxidants | +19 | +86 | +79 | +75 | +76 | +76 | +76 |
| Phenols | k.A. | +157 | +119 | +109 | +96 | +84 | +96 |
| Protective dissolved substances | | | | | | | |
| Proline (Shoot) | +275 | +227 | +333 | +233 | +120 | +87 | +35 |
| Proline (Roots) | k.A. | +60 | +96 | +78 | +180 | +120 | +80 |
| Nutrient level | | | | | | | |
| Zinc | +33 | +16 | +105 | +34 | +56 | +56 | +56 |
| Si | +43 | +43 | +43 | +50 | +40 | +53 | +37 | k.A. = no details

Figure 4:
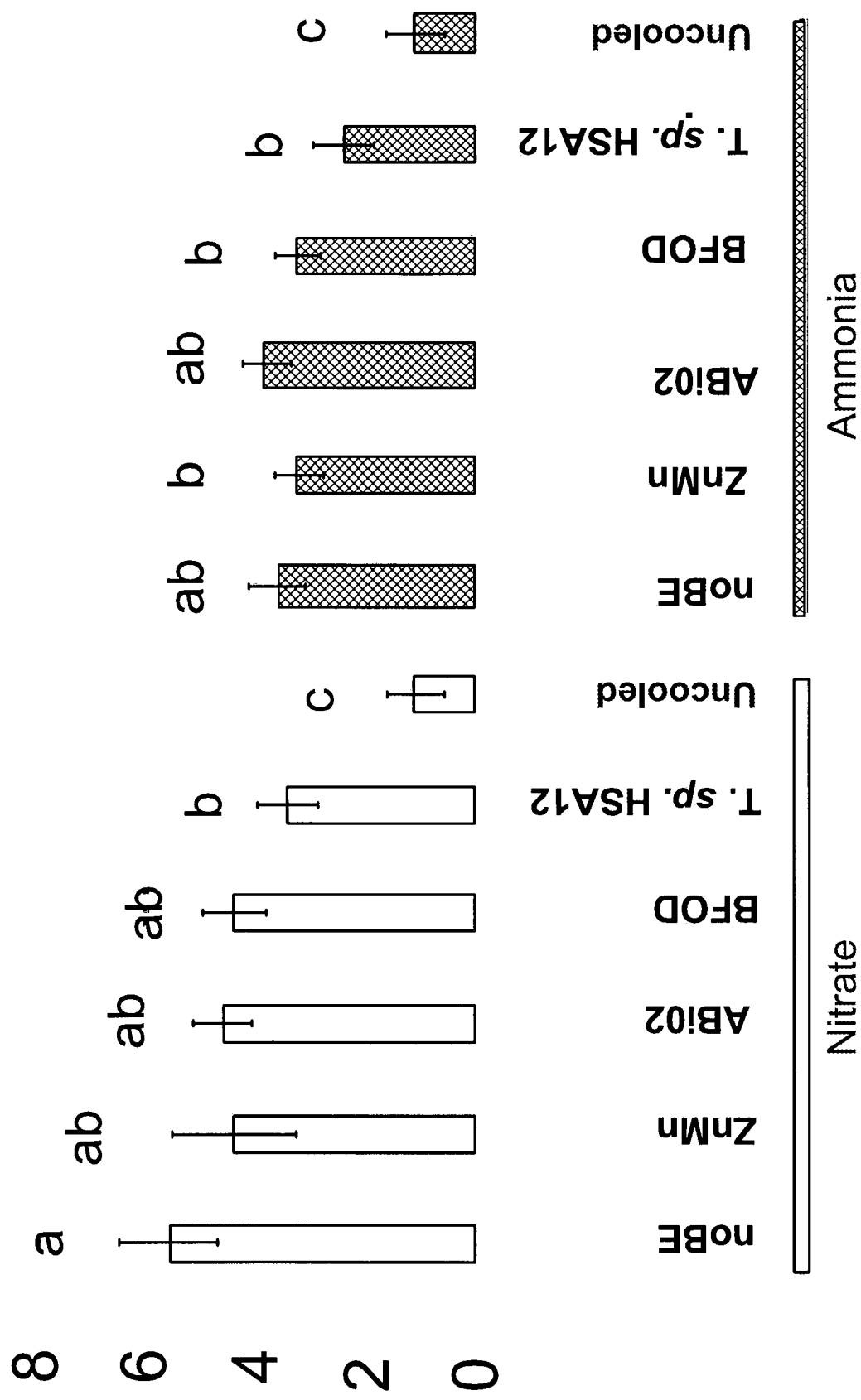
FIG. 4: a bar graph comparing the respective number of damaged leaves in the cultivation of maize under different conditions.

FIG. 4 shows the formation of leaf necrosis during cold stress in maize at a root temperature of 12° C. The number of damaged leaves when cultivating maize under various ingredients in the harvest of tomatoes of the variety "MOBIL" from Hungary due to the early flowering when *Trichoderma* sp. HSA12 is added. The letters above the columns indicate the significance, meaning that wherever the same letters appear, there are no significant differences and the level of significance is at least p<0.05.

FIG. 5A shows the concentrations of citric acid and maleic acid, and FIG. 5B shows the concentrations of glucose and fructose under four different conditions in each case, once in August and once in September. A control, a sample with the addition of *Trichoderma* sp. HSA12, abbreviated as BE, a sample with two bacterial additives, abbreviated as BR1 and BR2, and a sample with a combined addition of *Trichoderma* sp. HSA12 and one of the bacterial additives, BR2, are compared in the bar graphs.

The Induction of an earlier flowering time leads to an increase in valuable ingredients in crop plants, in the illustrated example in tomatoes. While the citric acid content of the controls in August was 220 mg per 100 g of fruit, the plant that was treated with *Trichoderma* sp. HSA12 had at this time already a significantly higher citric acid content with 250 mg per 100 g of fruit. In September, this difference was with 380 mg citric acid per 100 g fruit for the plants treated with *Trichoderma* sp. HSA12 was even greater compared to the control which had only 280 mg citric acid per 100 g fruit.

The maleic acid content in the fruits after treatment with *Trichoderma* sp. HSA was about the same in August and was slightly lower in September than in the control.

In August, as a result of the earlier flowering time, the glucose content in fruits from the plants treated with *Trichoderma* sp. HSA12 was with 850 mg per 100 g of fruit significantly higher than in the corresponding control, with the control having a glucose content of 480 mg per 100 g of fruit. In September, the glucose content in fruits from the plants treated with *Trichoderma* sp. HSA12 was with 560 mg per 100 g of fruit somewhat lower than in the corresponding control, where the value was 620 mg per 100 g of fruit.

Both in August and also in September, the values for fructose content in fruits from the plants treated with *Trichoderma* sp. HSA12 was significantly higher than in the control. The fructose content of the plants treated with *Trichoderma* sp. HSA12 was 400 mg per 100 g of fruit in August and 420 mg per 100 g of fruit in September, whereas the control values were 260 and 220 mg, respectively, per 100 g of fruit.

Figure 6B:
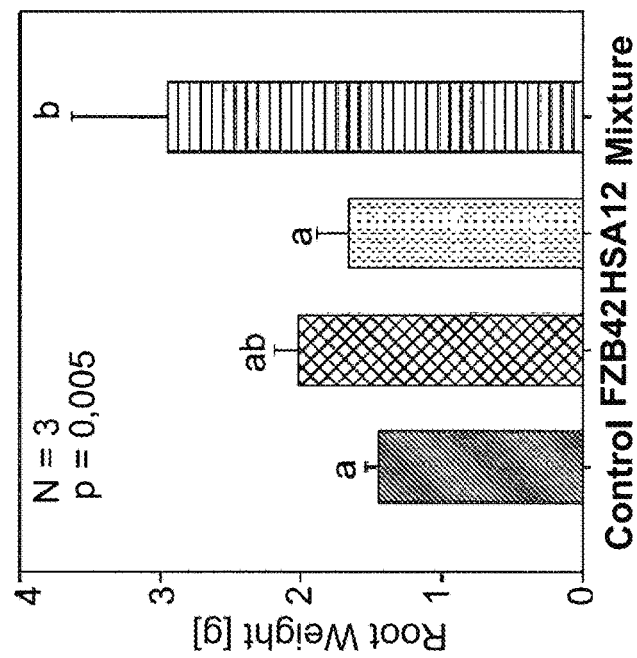
FIGS. 6A-B: the results of potted experiments with tomato plants of the type Harzfeuer in form of bar graphs.
Figure 6C:
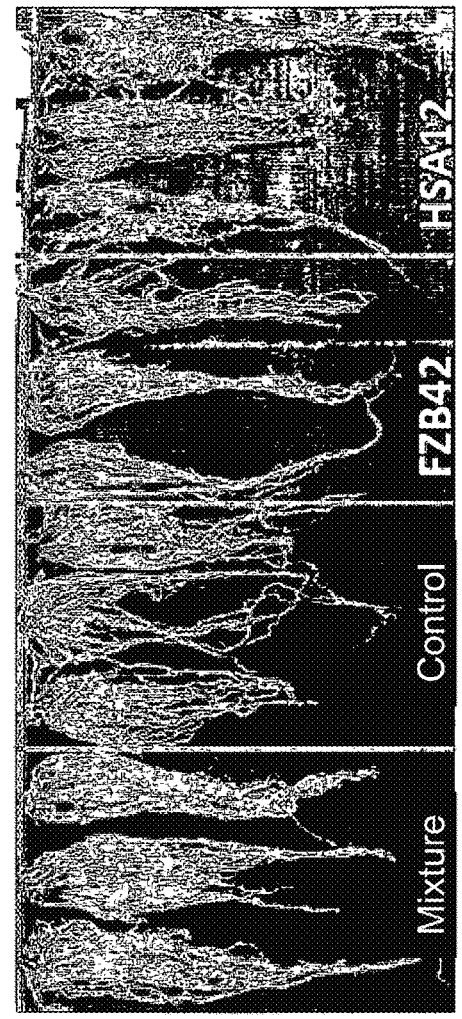
FIG. 6C: the results of potted experiments with tomato plants of the type Harzfeuer with reference to a photographic image.
Figure 6A:
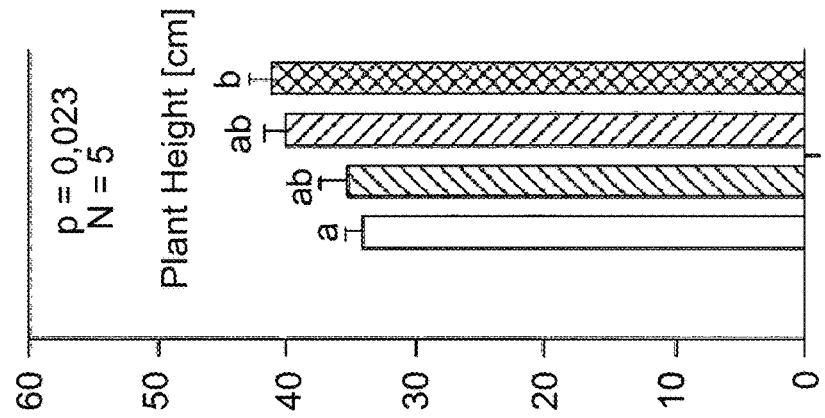

FIGS. 6A and 6B show in the form of bar charts the results of potted experiments with tomato plants of the type Harzfeuer. Plant roots were hereby each inoculated individually with T. sp. HSA12 and with the *Bacillus amyloliquedaciens* strain FZB42, respectively, and the results were compared, on the one hand, with a control and, on the other hand, with roots that were inoculated with a mixture of T. sp. HSA12 and FZB42. The strain FZB42 was purchased as the product RhizoVital™ from the company AbiTEP Berlin.

FIG. 6A shows a comparison of the plant heights in cm, while in FIG. 6B the root weights are compared with one another as a measurable variable for root growth.

The plant height, measured in cm, increases in the order control<FZB42<T. sp. HSA12<<<combination of T. sp. HSA12 and FZB42. The difference between the plant height of the plant treated with a combination of T. sp. HSA12 and FZB42 and the next greater plant height, namely the plant height of the plant treated only with T. sp. HSA12, is significantly greater than the respective differences between the individual comparison samples.

The root weight (dry weight) in g increases in the order of control<T. sp. HSA12<FZB42<<<combination of T. sp. HSA12 and FZB42. The difference between the root weight of the plant treated with a combination of T. sp. HSA12 and FZB 42 and the next higher root weight, namely that of the plant treated only with FZB, is significantly greater than the respective differences between the individual comparison samples. FIG. 6C shows photographic images of the roots of the differently treated plants and of the control.

In both cases, both in terms of plant height and in terms of root weight, no purely additive enhancement of the effectiveness of the two cultures contained in the mixture was observed; instead, the corresponding increases in plant height and root weight are clear signs of synergism.

Table 4a shows the sequences of the primer pairs for the determination of the genetic fingerprint of the fungal strain of the genus *Trichoderma* with the designation HSA12. Due to the availability of the complete genome sequence, T. sp. HSA12 is unambiguously characterized and unequivocally identifiable at any time, even when admixed to other products. A strain is characterized by its genome sequence. If the genome sequence is determined from two separate cultures and is identical, then this is by definition also the same strain. This would also apply if the strain were isolated from nature at a second time. But if the genome sequences exhibit even slight differences, then this is a different strain, another individual of the species. Since microorganisms and also micro-fungi have very few morphological characteristics, a gene segment of the ribosomal DNA (rDNA) is sequenced for associating micro-fungi to species or genera, and the obtained DNA sequence is compared with reference sequences stored in databases, which is known as DNA barcoding, from Schoch et al., Barcoding Consortium (2012), Nuclear ribosomal internal transcribed spacer as a universal DNA barcode marker for Fungi, PNAS 109 (16): 6241-6246. This analysis showed an association of HSA12 to the species *Trichoderma harzanium* with a probability of 98.8%. Another and more precise method, the comparison of the entire genome sequences (phylogenomics) of HSA12 with a *T. Harzanum* reference strain (Voucher Strain), only showed a match of 92% of all base pairs. However, a match of at least 97% is required in the case of fungi in order to be able to clearly associate the DNA sequences with a species. Therefore, HSA12 is definitely not *Trichoderma harzianum*, but possibly a previously unknown *Trichoderma* species or a known *Trichoderma* species whose genome sequence is not yet known. Therefore, the fungal strain is referred to as fungal strain HSA of the genus *Trichoderma* or as *Trichoderma* species HSA12, abbreviated as T. sp. HSA12.

Since at best species, but only genera can be determined with certainty using DNA barcoding, and since phylogenomics is very complex for the routine identification of individuals, and since only a few entire fungal genomes have been sequenced, the "genetic fingerprint" is used in routine diagnostics to identify individuals, see also Geistlinger et al., "SSR Markers for *Trichoderma* viruses: Their Evaluation and Application to identify and Quantify Root-Endophytic Strains", Diversity 2015, 7, 360-384. So-called hypervariable genome sections, so-called simple ones, are hereby used, so-called simple sequence repeats (SSR), also called microsatellites or SSR markers. Consequently, hypervariable genome segments from the T. sp. HSA12 genome are analyzed and a genetic fingerprint is generated. This genetic fingerprint serves, on the one hand, to again recognize the individual T. sp. HSA12 and, on the other hand, as an exclusion criterion for differentiating from other individuals from the same species or genus.

The genetic fingerprint is created using the polymerase chain reaction (PCR). To this end, the corresponding hypervariable genome segments, also called SSR markers, are amplified at each of the fifteen HSA12 loci. A pair of so-called primers, referred to below as a primer pair, defines the starting point of DNA synthesis on each of the two single strands of DNA, thereby delimiting the region to be replicated on both sides. The specified section is then replicated with the help of DNA polymerase, thereby amplifying the DNA sequence sections. The set of fifteen primer pairs used, referred to below as the primer set, is specific for the corresponding genome segments of the fungal strain *Trichoderma* sp. HSA12. Table 4a lists the thirty primer sequences with the corresponding SEQ.-numbers 1 to 30, of which two consecutive sequences in the sequence numbering (SEQ-NO.) form a primer pair.

The fragment length of the respective genome segments was determined at a total of fifteen HSA12 loci (L1 to L15) with single sequence repeats (SSRs), corresponding to the sequences with the SEQ-ID-NO. 31 to 45, by polymerase chain reaction (PCR) and compared with other *Trichoderma* products. This combination of fragment lengths according to Table 4b, given in base pairs (bp), was not obtained in any other isolate. Table 4b also lists the altogether fifteen repeating sequences with SEQ-ID-NO. 31 to 45 and the respective number of sequence repetitions (repeat number) in the genome sections which are amplified by the altogether fifteen primer pairs formed from the primer sequences with the SEQ-ID-NO. 1 to 30.

TABLE 4b

| SEQ-ID-NO. | Tm [°0] | Locus | SEQ-ID-NO. | Repeat Number | Fragment Length [bp] |
|---|---|---|---|---|---|
| 1 | 60.10 | L1 | 31 | $(GAA)_{11}$ | 488 |
| 2 | 60.30 | | | | |
| 3 | 60.19 | L2 | 32 | $(TCC)_{12}$ | 426 |
| 4 | 59.73 | | | | |
| 5 | 59.70 | L3 | 33 | $(CAT)_{11}$ | 365 |
| 6 | 60.29 | | | | |
| 7 | 60.20 | L4 | 34 | $(CTT)_{15}$ | 492 |
| 8 | 60.04 | | | | |
| 9 | 60.14 | L5 | 35 | $(AGT)_{13}$ | 204 |
| 10 | 60.31 | | | | |
| 11 | 59.91 | L6 | 36 | $(GAAGTGAAG)_{7}$ | 236 |
| 12 | 59.99 | | | | |
| 13 | 59.81 | L7 | 37 | $(TTTGT)_{8}$ | 287 |
| 14 | 69.99 | | | | |

TABLE 4a

| Loci | Primer designations | SEQ-ID-No. | Primer sequences 5'-3' |
|---|---|---|---|
| L1 | HSA12S51GAA11f | 1 | 5'-CGGATGTGAGACGCAATATG-3' |
| | HSA12S51GAA11r | 2 | F-CAACAGCGAAGTGTTGATGG-3' |
| L2 | HSA12S52TCC12f | 3 | F-TCAACTICGCCCTCATTTTC-3' |
| | HSA12S52TCC12r | 4 | 5'-CGATCTCGAAGCTGACACAG-3' |
| L3 | HSA12S53CAT11f | 5 | 5'-GTCTGGCTACATTGGCCTTC-3' |
| | HSA12S53CAT11r | 6 | 5'-AGACGGAGGGGGAGATTATG-3' |
| L4 | HSA12S54CTT15f | 7 | 5'-TCCTCCTCAATCACCTTTGC-3' |
| | HSA12554CTT15r | 8 | 5'-TTTCCCGAAGAAATCACAGG-3' |
| L5 | HSA12S55AGT13f | 9 | 5'-GCCACAGAGAGAAGCCAGTC-3' |
| | HSA12S55AGT13r | 10 | 5'-GCGTCATGTCCCCATCTATC-3' |
| L[6] | HSA12S56GAAGTGAAG7f | 11 | 5'-TTTCTTCGTGTTTCCCCATC-3' |
| | HSA12S56GAAGTGAAG7r | 12 | 5'-GACAAAGAAGCCGAGGACAG-3' |
| L[7] | HSA12S56GTTTGT8f | 13 | 5'-ATCAATAGACGGGGCATACG-3' |
| | HSA12S56GTTTGT8r | 14 | 5'-CGAAAAGAGAGCCAAAAACG-3' |
| L8 | HSA12S58CT14f | 15 | 5'-GGAGAACGAAGCTTGACCTG-3' |
| | HSA12S58CT14r | 16 | 5'-TATACCCCGCCTCAACAGTC-3' |
| L9 | HSA12S59TA12f | 17 | 5'-TGGIGGIGIGTACGAAATGG-3' |
| | HSA12S59TA12r | 18 | 5'-GGCATCGTAGCGAAGTAAGC-3' |
| L10 | HSA12S60TCAGG5f | 19 | 5'-TCCAAACCCTGACTGAGGTC-3' |
| | HSA12S60TCAGG5r | 20 | 5'-AGATGCAGATCGTCGTGTTG-3' |
| L11 | HSA12S60CAG10f | 21 | 5'-CTGCCTCTCCAGAACACTCC-3' |
| | HSA12S60CAG10r | 22 | 5'-CATTATAAGGGGCCACAACG-3' |
| L12 | HSA12S61AGG6f | 23 | 5'-TACAGCACGAAGACGCTCTC-3' |
| | HSA12S61AGG6r | 24 | 5'-AACAGCGACCAAGCATAACC-3' |
| L13 | HSA12S63TGC7f | 25 | 5'-CTGTCGAGATTGCTGCTGAG-3' |
| | HSA12S63TGC7r | 26 | 5'-ATGTACTTTTCCGCGTCCAG-3' |
| L14 | HSA12S66AGTGCC11f | 27 | 5'-TTCAACAGCGTCAACCTCAG-3' |
| | HSA12S66AGTGCC11r | 28 | 5'-CCGGATTTATTTTGGTGGTG-3' |
| L15 | HSA12S66AT17f | 29 | 5'-CATTTGGGGTGGGTATTCTG-3' |
| | HSA12S66AT17r | 30 | 5'-ATTGTCACCGATGGAGGAAG-3' |

TABLE 4b-continued

| SEQ-ID-NO. | Tm [°0] | Locus | SEQ-ID-NO. | Repeat Number | Fragment Length [bp] |
|---|---|---|---|---|---|
| 15 | 59.99 | L8 | 38 | $(GT)_{14}$ | 289 |
| 16 | 59.96 | | | | |
| 17 | 60.28 | L9 | 39 | $(TA)_{12}$ | 468 |
| 18 | 60.01 | | | | |
| 19 | 60.09 | L10 | 40 | $(TCAGG)_5$ | 481 |
| 20 | 59.86 | | | | |
| 21 | 59.99 | L11 | 41 | $(CAG)_{10}$ | 460 |
| 22 | 60.20 | | | | |

TABLE 4b-continued

| SEQ-ID-NO. | Tm [°0] | Locus | SEQ-ID-NO. | Repeat Number | Fragment Length [bp] |
|---|---|---|---|---|---|
| 23 | 59.34 | L12 | 42 | $(AGG)_6$ | 473 |
| 24 | 60.14 | | | | |
| 25 | 59.88 | L13 | 43 | $(TGC)_7$ | 401 |
| 26 | 60.13 | | | | |
| 27 | 60.02 | L14 | 44 | $(AGTGCC)_{11}$ | 306 |
| 28 | 60.05 | | | | |
| 29 | 60.04 | L15 | 45 | $(AT)_{17}$ | 33 |
| 30 | 59.93 | | | | |

What is claimed is:

1. A method for at least one of promoting plant growth, stabilizing plant growth and increasing yields of crop plants, comprising:

inoculating one or more of the group consisting of plant soil, plant roots and above-ground parts of a plant with fungal strain *Trichoderma* HSA12, which was deposited on Jan. 12, 2018 under the patent deposit number DSM 32722 at the Leibniz institute DSMZ—German Collection of Microorganisms and Cell Cultures GmbH, or spores thereof.

2. The method according to claim 1, wherein plant growth is suffering under abiotic stress, selected from the group consisting of drought stress, cold stress and oxidative stress.

3. The method according to claim 2, wherein the abiotic stress results from a sowing or planting date for a crop plant that is advanced or delayed in relation to a respective region.

4. The method according to claim 3, wherein the crop plant is an agricultural plant.

5. The method according to claim 4, wherein the agricultural plant is selected from the group consisting of tomato plants, maize plants and soybean plants.

6. A method for improving structure and health of a soil, or for decontaminating or remediating a soil containing toxic organic substances, comprising:

inoculating the soil with fungal strain *Trichoderma* HSA12, which was deposited on Jan. 12, 2018 under the patent deposit number DSM 32722 at the Leibniz institute DSMZ—German Collection of Microorganisms and Cell Cultures GmbH, and cultivating the *Trichoderma* HSA12 in the soil.

7. The method of claim 1, wherein inoculating the soil, the plant roots and the above-ground parts of the plant is carried out with a composition comprising the *Trichoderma* HSA12 and additional microorganisms or biological fertilizers and adjuvants.

8. A method for stabilizing or resettling wild plant populations, comprising:

inoculating soil of the wild plant population, and at least one of roots of the wild plant population and above-ground parts of the wild plant population, with fungal strain *Trichoderma* HSA12, which was deposited on Jan. 12, 2018 under the patent deposit number DSM 32722 at the Leibniz institute DSMZ—German Collection of Microorganisms and Cell Cultures GmbH.

9. A method for improving a crop soil or a body of water containing toxic organic substances, comprising:

inoculating the soil or the body of water with fungal strain *Trichoderma* HSA12, which was deposited on Jan. 12, 2018 under the patent deposit number DSM 32722 at the Leibniz institute DSMZ—German Collection of Microorganisms and Cell Cultures GmbH, and cultivating the *Trichoderma* HSA12 in the crop soil or the body of water.

10. A method for improving structure and health of a body of water containing toxic organic substances, comprising:

inoculating the body of water with fungal strain *Trichoderma* HSA12, which was deposited on Jan. 12, 2018 under the patent deposit number DSM 32722 at the Leibniz institute DSMZ—German Collection of Microorganisms and Cell Cultures GmbH, and cultivating the *Trichoderma* HSA12 in the body of water.

* * * * *